(12) United States Patent
Shirota

(10) Patent No.: US 6,646,105 B2
(45) Date of Patent: Nov. 11, 2003

(54) PROCESS FOR TREATING BY-PRODUCT OF POLYARYLENE SULFIDE

(75) Inventor: Daigo Shirota, Chiba (JP)

(73) Assignees: Petroleum Energy Center, Tokyo (JP); Idemitsu Petrochemical Co., Ltd., Tokyo (JP)

( * ) Notice: Subject to any disclaimer, the term of this patent is extended or adjusted under 35 U.S.C. 154(b) by 63 days.

(21) Appl. No.: 10/105,368

(22) Filed: Mar. 26, 2002

(65) Prior Publication Data

US 2002/0143140 A1 Oct. 3, 2002

(30) Foreign Application Priority Data

Mar. 30, 2001 (JP) ........................................ 2001-098373

(51) Int. Cl.⁷ .............................................. C08G 75/14
(52) U.S. Cl. ...................... 528/388; 528/488; 528/491; 528/492; 528/502 R; 528/502 C; 528/503
(58) Field of Search ................................ 528/388, 488, 528/491, 492, 502 R, 502 C, 503

(56) References Cited

U.S. PATENT DOCUMENTS

| | | | |
|---|---|---|---|
| 4,810,773 A | * | 3/1989 | Ogata et al. |
| 4,840,986 A | * | 6/1989 | Inoue et al. |
| 4,919,911 A | * | 4/1990 | Shirota et al. |
| 5,241,043 A | * | 8/1993 | Senga |
| 5,278,283 A | * | 1/1994 | Miyoshi et al. |

\* cited by examiner

*Primary Examiner*—Duc Truong
(74) *Attorney, Agent, or Firm*—Oblon, Spivak, McClelland, Maier & Neustadt, P.C.

(57) ABSTRACT

There is disclosed a process for treating a by-product salt from a polyarylene sulfide which comprises treating a solid mixture containing an aprotic organic solvent and the by-product salt that is formed in the case of producing the polyarylene sulfide by subjecting an alkali metal sulfide and a dihalogenated aromatic compound to polymerization condensation reaction in the aprotic organic solvent, characterized in that the aprotic organic solvent is recovered by dry treating the solid mixture by the use of a dryer having a self-cleaning property. It is enabled by the above process to efficiently recover the aprotic organic solvent, and thereby produce the objective polyarylene sulfide at a lower cost.

10 Claims, No Drawings

PROCESS FOR TREATING BY-PRODUCT OF POLYARYLENE SULFIDE

BACKGROUND OF THE INVENTION

1. Field of the Invention

The present invention relates to a process for treating a by-product salt that is formed as a by-product in the production of a polyarylene sulfide (hereinafter sometimes referred to as "PAS"). More particularly, it pertains to a process for treating a by-product salt which comprises treating the by-product salt that is formed as a by-product in the production of the polyarylene sulfide, and efficiently recovering an aprotic organic solvent as a reaction solvent.

2. Description of the Related Arts

A polyarylene sulfide, especially polyphenylene sulfide is known as an engineering plastic which is excellent in mechanical strength, heat resistance and the like and which has good electrical characteristics and high rigidity. Thus it is widely employed as a variety of materials such as electronic machinery parts and electrical machinery parts.

As a process for producing polyarylene sulfide, there has heretofore been employed in general, a process in which a dihalogenated aromatic compound such as p-dichlorobenzene and a sodium salt such as sodium sulfide are reacted with each other in the presence of an aprotic organic solvent such as N-methyl-2-pyrrolidone (hereinafter sometimes abbreviated to "NMP") to effect a polymerization condensation reaction.

In the above-mentioned process however, a sodium halogenide as a by-product, which is insoluble in a solvent such as NMP, is incorporated in a resin, as a result, the removal of the solvent by cleaning has been far from easy. Moreover, it has been extremely difficult to continuously treat at a high temperature, a polymer and sodium halogenide as a by-product that are formed in the aforesaid process.

Under such circumstances, it has been found that continuous treatment of the polymer at a high temperature is made possible by a method in which the polymerization condensation reaction is conducted by using a lithium salt in place of the sodium salt in the presence of NMP as a solvent so as to form a lithium halogenide, since the lithium halogenide is soluble in a number of aprotic organic solvents such as NMP as a polymerization solvent, thereby enabling it comparatively easy to lower the concentration of lithium in the resin (refer to Japanese Patent Application Laid-Open No. 207027/1995 (Heisei 7).

In the above-mentioned process however, lithium sulfide as a starting raw material for polymerization reaction is obtained, for instance, by reacting lithium chloride with sodium hydroxide to obtain lithium hydroxide, reacting the resultant lithium hydroxide with hydrogen sulfide to obtain lithium hydrosulfide, and subjecting the resultant lithium hydrosulfide to hydrogen sulfide removing reaction. In such reaction system, when lithium chloride is reacted with sodium hydroxide, sodium chloride is formed as a reaction by-product. The resultant sodium chloride, when being subjected to polymerization reaction as such, gives rise to the problem same as the foregoing. Accordingly, it is customary that slurry solution containing lithium hydrosulfide thus formed is subjected to solid-liquid separation to separate it into a solvent portion containing lithium hydrosulfide and a solid matter containing a by-product salt such as sodium chloride, and the solvent portion is subjected to next lithium sulfide synthesis step.

However, when an attempt is made to recover the solvent by drying the solid mixture containing sodium chloride as mentioned above, there is caused a problem in that the solvent is unlikely to be separated because of markedly small particle diameter of the sodium chloride contained in the foregoing solid matter. In addition, in the case of recycling the solvent phase or the like formed by solid-liquid separation of PAS polymerization reaction mixture to use as a starting material, there is also caused a problem in that a small amount of an oligomer present in the solid mixture unfavorably increases the viscosity of the solvent phase. Moreover, another problem is raised thereby in that the use of a conventional dryer such as a disc dryer increases the viscosity of an object to be dried during the course of drying, the object adheres to machinery and equipment, and thereby makes it impossible to continue drying treatment, whereby the objective solvent recovery is made insufficient.

SUMMARY OF THE INVENTION

It is a general object of the present invention to provide a process for producing a polyarylene sulfide at a low cost by efficiently recovering an aprotic organic solvent as a reaction solvent in the case of producing the polyarylene sulfide under such circumstances.

Other objects of the present invention will become obvious from the text of the specification hereinafter disclosed.

In such circumstances, intensive extensive research and investigation were accumulated by the present inventors in order to achieve the above-mentioned objects. As a result, it has been found that the objects of the present invention can be achieved by dry treating a solid mixture containing an aprotic organic solvent and a by-product salt by using a dryer having a specific drying system, said salt being formed in the case of producing a polyarylene sulfide from an alkali metal sulfide and a dihalogenated aromatic compound in the aprotic organic solvent. The present invention has been accomplished on the basis of the foregoing findings and information.

Specifically, the present invention provides a process for treating a by-product salt from a polyarylene sulfide which comprises treating a solid mixture containing an aprotic organic solvent and the by-product salt that is formed as a by-product in the case of producing the polyarylene sulfide by subjecting an alkali metal sulfide and a dihalogenated aromatic compound to polymerization condensation reaction in the aprotic organic solvent, characterized in that the foregoing aprotic organic solvent is recovered by dry treating the aforesaid solid mixture by the use of a dryer having a self-cleaning property.

DESCRIPTION OF THE PREFERRED EMBODIMENTS

In the following, more detailed description will be given of the present invention.

The polymerization condensation reaction between an alkali metal sulfide and a dihalogenated aromatic compound is put into practice in an aprotic organic solvent.

Examples of the aprotic organic solvent include in general, aprotic organic polar solvents such as amide compounds, lactam compounds, urea compounds, organosulfur compounds and cyclic organophosphorus compounds.

The above-mentioned amide compounds among aprotic organic polar solvents are exemplified by N,N-dimethylformamide; N,N-diethylformamide; N,N- dimethylacetoamide; N,N-diethylacetoamide; N,N-dipropylacetoamide; N,N-dimethylbenzoic acid amide, etc.

The aforesaid lactam compounds are exemplified by N-alkyl-caprolactam such as caprolactam; N-methylcaprolactam; N-ethylcaprolactam; N-isopropylcaprolactam; N-isobutylcaprolactam; N-n-propylcaprolactam; N-n-butylcaprolactam; and N-cyclohexylcaprolactam; N-methyl-2-pyrrolidone(NMP); N-ethyl-2-pyrrolidone; N-isopropyl-2-pyrrolidone; N-isobutyl-2-pyrrolidone; N-n-propyl-2-pyrrolidone; N-n-butyl-2-pyrrolidone; N-cyclohexyl-2-pyrrolidone; N-methyl-3-methyl-2-pyrrolidone; N-ethyl-3-methyl-2-pyrrolidone; N-methyl-3,4,5-trimethyl-2-pyrrolidone; N-methyl-2-piperidone; N-ethyl-2-piperidone; N-isopropyl-2-piperidone; N-methyl-6-methyl-2-piperidone; N-methyl-3-ethyl-2-piperidone, etc.

The aforesaid urea compounds are exemplified by tetramethylurea; N,N'-dimethylethyleneurea; N,N'-dimethylpropyleneurea, etc.

The aforesaid organosulfur compounds are exemplified by dimethylsulfoxide; diethylsulfoxide; diphenylsulfone; 1-methyl-1-oxosulfolane; 1-ethyl-1-oxosulfolane; 1-phenyl-1-oxosulfolane etc.

The aforesaid cyclic organophosphorus compounds are exemplified by 1-methyl-1-oxophosfolane; 1-n-propyl-1-oxophosfolane; 1-phenyl-1-oxophosfolane, etc.

Any of the above-exemplified aprotic organic polar solvent can be used alone or by mixing with at least one other or by mixing with a solvent which is not cited above and does not impair the object of the present invention so as to enable the mixture to be used as the foregoing aprotic organic solvent. Of the various aprotic organic solvents as exemplified above are preferable N-alkylcaprolactam and N-alkylpyrrolidone, among which N-methyl-2-pyrrolidone (NMP) is particularly preferable.

The polyarylene sulfide mentioned in the present invention is, for instance, a polymer having at least 70 mole % of the repeating unit represented by —Ar—S— wherein Ar is an arylene group. A typical example includes an polyarylene sulfide having at least 70 mole % of the repeating unit represented by the following general formula (I):

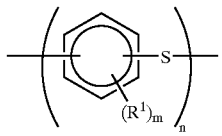

wherein $R^1$ is a substituent selected from an alkyl group having at most 6 carbon atoms, an alkoxy group, a phenyl group, a carboxylic acid, a metal salt thereof, an amino group, a nitro group and a halogen atom such as a fluorine atom, chlorine atom and bromine atom; m is an integer from 0 to 4; and n denotes degree of polymerization and is in the range of 10 to 200.

The known polyarylene sulfide is generally classified by its production process into that having a substantially linear molecular structure without a branched or crosslinked structure, and that having a branched or crosslinked structure. In the production process relating to the present invention, any of the polyarylene sulfide is effectively usable.

The polyarylene sulfide is exemplified by a homopolymer or a copolymer each having as the repeating unit, at least 70 mole %, preferably 80 mole % of p-phenylene sulfide. Examples of constituting unit of the copolymer include m-phenylene sulfide unit; o-phenylene sulfide unit; p, p'-diphenyleneketone sulfide unit; p, p'-diphenylenesulfone sulfide unit; p,p'-biphenylenesulfide unit; p,p'-diphenyleneether sulfide unit; p,p'-diphenylenemethylene sulfide unit; p,p'-diphenylenecumenyl sulfide unit; and naphthylene sulfide unit. Moreover, as a polyarylene sulfide that can be an object relating to the present invention, mention can be made in addition to the foregoing substantially linear polymer, of a branched or crosslinked polyarylene sulfide in which a small amount of monomer having at least three functional groups as a part of monomers is polymerized, and a blended polymer in which the polyarylene sulfide just cited is blended with the foregoing substantially linear polymer.

In the above-mentioned polymerization condensation reaction use is made of as starting raw materials, an alkali metal sulfide and a dihalogenated aromatic compound. Examples of the dihalogenated aromatic compound include dihalogenated benzene such as m-dihalogenated benzene and p-dihalogenated benzene, alkyl-substituted dihalogenated benzene, cycloalkyl-substituted dihalogenated benzene and the like such as 2,3-dihalogenated toluene; 2,5-dihalogenated toluene; 2,6-dihalogenated toluene; 3,4-dihalogenated toluene; 2,5-dihalogenated xylene; 1-ethyl-2, 5-dihalogenated benzene; 1,2,4,5-tetramethyl-3,6-dihalogenated benzene; 1-n-hexyl-2,5-dihalogenated benzene; and 1-cyclohexyl-2,5-dihalogenated benzene, aryl-substituted dihalogenated benzene such as 1-phenyl-2,5-dihalogenated benzene; 1-benzyl-2,5-dihalogenated benzene; and 1-p-toluyl-2,5-dihalogenated benzene, dihalobiphenyl such as 4,4'-dihalobiphenyl, dihalogenated naphthalene such as 1,4-dihalonaphthalene; 1,6-dihalonaphthalene; and 2,6-dihalonaphthalene, and the like.

On the other hand, examples of the alkali metal sulfide include sodium sulfide, lithium sulfide and potassium sulfide, of which each may be used alone or in combination with at least one other. Further, the alkali metal sulfide may be used in combination with an alkaline earth metal sulfide and/or an other sulfur source. In the process according to the present invention, lithium sulfide is preferable in particular. For instance, lithium sulfide can be produced by reacting lithium hydroxide and hydrogen sulfide in an aprotic organic solvent to form lithium hydrosulfide, and subsequently hydrodesulfurizing the resultant reaction liquid.

That is to say, lithium sulfide is synthesized by the hydrodesulfurization reaction of lithium hydrosulfide according to the following chemical equation.

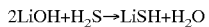

The lithium hydroixde to be used therein is obtained by reacting sodium hydroixde with lithium chloride. The present invention relates to a process for effectively treating a by-product salt such as sodium chloride which is formed as a by-product in this reaction. The lithium chloride to be used as a starting raw material in the aforesaid reaction may be newly added in whole amount, but it is possible to use lithium chloride contained in a solvent phase which is obtained by solid-liquid separation of PAS polymerization reaction mixture as it is or by properly refining the same.

The hydrogen sulfide is not specifically limited, but there is usable, for instance, hydrogen sulfide in an off gas which is generated from a petroleum refinery.

The molar ratio of hydrogen sulfide to lithium hydroixde that are to be used in the treatment (molar ratio of hydrogen sulfide/lithium hydroixde) is usually at least 1.0 (mole/mole), especially at least 1.05 (mole/mole).

In carrying out the above-mentioned reaction, for instance, a reaction vessel is charged inside with the foregoing aprotic organic solvent and lithium hydroixde, and hydrogen sulfide is blown into the resultant charged liquid to react therewith. In this case, the reaction may be put into practice by blowing hydrogen sulfide in advance into the aprotic organic solvent to dissolve the same, and by mixing lithium hydroixde with the solvent thus prepared.

In the present invention, hydrogen sulfide may be blown at atmospheric pressure or under pressure. The blowing time and blowing rate are not specifically limited. A method for blowing hydrogen sulfide is not specifically limited, but may be for instance, a conventionally used method in which an aprotic organic solvent is incorporated with lithium hydroixde under stirring, and further with gaseous hydrogen sulfide by means of bubbling. This method can be carried out in a continuous system in the absence or presence of water. The reaction temperature is in the range of preferably 80 to 120° C., particularly preferably 90 to 110° C.

Preferably, the reaction time is at least a value that is obtained by dividing a necessary amount of hydrogen sulfide calculated from the aforesaid molar ratio of hydrogen sulfide/lithium hydroixde by a velocity which prevents hydrogen sulfide to be supplied from blowing through the solvent.

By feeding hydrogen sulfide in such a manner, the lithium hydroixde that had been present in solid form in the system is converted into lithium hydrosulfide, which is dissolved in the liquid portion of the system.

In the present invention, after the formation of lithium hydrosulfide, the slurry containing the lithium hydrosulfide and a by-product salt such as sodium chloride is subjected to solid-liquid separation by means of centrifugal separation, whereby the slurry is separated into a solvent phase containing lithium hydrosulfide and a by-product salt such as sodium chloride.

The amounts of the by-product salt such as sodium chloride and the aprotic organic solvent in the solid mixture depend upon a variety of conditions such as the types of the starting raw materials and the solvent, reaction conditions and solid-liquid separation conditions. In general, the contents of sodium chloride and the aprotic organic solvent are 40 to 60% by weight, and 60 to 40% by weight, respectively. The particle diameter of sodium chloride in solid form is approximately 5 to 10 micrometer.

The solvent portion containing lithium hydrosulfide that has been separated by solid-liquid separation is utilized for synthesis reaction of lithium sulfide in the next step, and the solid mixture is dried to remove and discard the by-product salts such as solid sodium chloride contained therein. The aprotic organic solvent that has been evaporated and separated through the drying is recovered and reused by being recycled to the synthesis step for lithium hydrosulfide. The drying efficiency can be enhanced by rinsing, prior to the drying, the aprotic organic solvent which contains polymerized by-products such as PAS oligomer stuck to sodium chloride and the like with a refined aprotic organic solvent.

A drying treatment of solid mixture containing by-product salts such as sodium chloride by the use of a dryer such as a conventionally used disc dryer gives rise to an unfavorable state in that the viscosity of the object to be dried increases during drying en route, and the object adheres to machinery and equipment, thereby making the drying treatment impossible to continue, whereby the solvent contained in the solid matter can not be sufficiently recovered.

As the countermeasure thereaginst in the present invention, the foregoing solid matter to be dried is subjected to a drying treatment by the use of a dryer having a self-cleaning property, so that the adhesion of the object to be dried to machinery and equipment is prevented to effectively perform the drying, whereby the solvent contained in the solid matter is removed in high efficiency.

The dryer having a self-cleaning property is exemplified by a horizontal twin shaft dryer the construction of which is such that each shaft is equipped with a paddle, and the paddles that are attached to the shafts rotate in the same or different direction, keeping a slight clearance therebetween (self-cleaning property). There is usually preferably usable a hollow paddle which has an automatically conveyable shape and can circulate inside a heating medium because of a large heat transfer area per unit volume. The twin shaft may be equipped with screws having conveyable mechanism in addition to the paddles. The screws are preferably of a hollow type capable of circulating inside a heating medium as is the case with the paddles.

The above-mentioned dryer is capable of heating an object by passing a heating medium through the foregoing paddles and screws as well as a shell-heating jacket, thereby enabling uniform heating with a large heat transfer area. In addition, by evacuating the inside of the dryer, it is made possible to effectively evaporate the solvent contained in the solid matter as the object to be dried.

There is usable as the dryer having such a self-cleaning property, a marketed dryers manufactured by Kurimoto Ltd. under the trade name "SCP series" and "KRC series" and a marketed dryer manufactured by Mitsubishi Heavy Industries, Ltd. under the trade name "SCR series" and the like.

As the conditions in the above-mentioned drying treatment, the temperature of the object to be dried is in the range of 120 to 250° C., preferably 140 to 220° C., and the pressure thereof is atmospheric pressure to 0.001 MPa, preferably atmospheric pressure to 0.01 MPa. The drying treatment time, which depends upon the temperature and pressure of the drying treatment and type of dryer, can not be unequivocally determined, but one to 10 hours is generally sufficient.

In the present invention, by subjecting the solid matters to drying treatment using the dryer having a self-cleaning property, it is made possible to prevent the object to be dried from adhering to the machinery and equipment, to carry out continuous drying for a long time, decrease the content of solvent in the dried object as low as 1000 ppm or lower, and thus efficiently recover the solvent. As opposed to the foregoing, a conventional dryer such as disc dryer causes the object to be dried to adhere to the machinery and equipment in a short period of time, thus obliging the operation to discontinue and besides, brings about a large solvent loss by leaving the solvent as large as usually 5% or more by weight in the object to be dried.

In the present invention, a comonomer, a branching agent, an end terminator and the like may be combinedly used with the above-mentioned dihalogenated aromatic compound to the extent that the effect thereof is not impaired thereby. Examples of the comonomer include 2,3-dichlorophenol; 2,3-dibromophenol; 2,4-dichlorophenol; 2,4-dibromophenol; 2,5-dichlorophenol; 2,5-dibromophenol; 2,4-dichloroaniline; 2,4-dibromoaniline; 2,5-dichloroaniline; 2,5-dibromoaniline; 3,3'-dichloro-4,4'-diaminobiphenyl; 3,3'-dibromo-4,4'-diaminobiphenyl; 3,3'-dichloro-4,4'-dihydoxybiphenyl; 3,3'-dibromo-4,4'-dihydoxybiphenyl; di(3-chloro-4-amino)phenylmethane;

m-dichlorobenzene; m-dibromobenzene; o-dichlorobenzene; o-dibromobenzene; 4,4'-dichlorodiphenyl ether; and 4,4'-dichlorodiphenylsulfone. Examples of the branching agent include 1,2,4-trichlorobenzene; 1,3,5-trichlorobenzene; and 1,2,3-trichlorobenzene.

Examples of the end terminator include a halogenated phenol such as p-bromophenol; m-bromophenol; o-bromophenol; p-chlorophenol; m-chlorophenol; o-chlorophenol; p-fluorophenol; m-fluorophenol; o-fluorophenol; p-iodophenol; m-iodophenol; o-iodophenol. Of these, p-bromophenol and p-chlorophenol are preferable.

With regard to the proportion of the starting raw materials to be used in the process according to the present invention, the molar ratio of the dihalogenated aromatic compound to the alkali metal sulfide is preferably 0.8 to 1.2, more preferably 0.9 to 1.1, particularly preferably 0.95 to 1.05. When the molar ratio is outside the range of 0.8 to 1.2, there exists a fear of failure to obtain a polyarylene sulfide having a high molecular weight.

The polymerization condensation reaction of PAS may be put into practice by one stage reaction at a temperature in the range of 230 to 290° C., approximately, preferably 240 to 280° C., more preferably 250 to 270° C., or by the combination of the above-mentioned polymerization condensation and a preliminary polymerization prior thereto at a temperature in the range of 180 to 230° C., preferably 190 to 220° C., more preferably 195 to 215° C. The polymerization condensation reaction time is usually 0.5 to 10 hours, preferably 1.0 to 10 hours, more preferably 1.5 to 10 hours. The polymerization condensation reaction time, when being less than 0.5 hour, causes a fear of insufficient reaction resulting in failure to assure a sufficiently high molecular weight, whereas the reaction time, when being more than 10 hour, does not exert the working effect in proportion to the reaction time. The polymerization condensation vessel may be either a batchwise system or a continuous system, but the latter is preferable in the present invention.

In summarizing the working effects of the present invention it is enabled in producing a polyarylene sulfide to efficiently recover an aprotic organic solvent as a reaction solvent and at the same time, to produce the polyarylene sulfide at a lower cost.

In what follows, the present invention will be described in more detail with reference to working examples, which however shall never limit the present invention thereto.

EXAMPLE 1

An aqueous solution of sodium hydroxide with a concentration of 48% by weight in an amount of 118 kg was added to 545 kg of a starting raw material in liquid form which had been generated from a PAS production pilot plant as polymer cleaning solution (chemical composition: 11% by weight of LiCl, 0.6% by weight of PAS oligomer and the balance being NMP). The slurry thus obtained was centrifuged to separate into solid and liquid. As a result, there was obtained 233 kg of solid cake containing 14% by weight of LiOH and 35% by weight of NaCl. The cake was added to 500 kg of NMP to be again slurried. In order to convert the LiOH to LiSH, a sufficient amount of $H_2S$ being 35 n-m$^3$ in total was blown into the resultant slurry, while stirring the same. The resultant slurry containing LiSH was centrifuged. As a result, there was obtained 158 kg of solid cake containing 51% by weight of NaCl. The cake was added to 500 kg of NMP to be again slurried. The resultant slurry was centrifuged with a result that 154 kg of solid cake containing 52% by weight of NaCl was obtained.

Subsequently, the solid cake was continuously vacuum dried by using a self-cleaning type dryer manufactured by Kurimoto Ltd. under the trade name "SC processor SCP series 100" in the conditions including a temperature of the object to be dried being 150° C., a heating medium temperature of 190° C., pressure of 14 kpa-abs and a starting material feed rate of 38 kg/hour. As a result, no trouble including the adhesion of solid matter to the machinery and equipment took place even after continuous running for a total of 3 hours, and the average content of NMP in the dried solid matter was 650 ppm.

EXAMPLE 2

The solid matter same as that in Example 1 was continuously vacuum dried by using a self-cleaning type dryer manufactured by Mitsubishi Heavy Industries Ltd. under the trade name "SCR 100" in the conditions including a temperature of the object to be dried being 150° C., a heating medium temperature of 190° C., pressure of 14 kpa-abs and a starting material feed rate of 38 kg/hour. As a result, no trouble including the adhesion of solid matter to the machinery and equipment took place even after continuous running for a total of 3 hours, and the average content of NMP in the dried solid matter was 550 ppm.

EXAMPLE 3

The solid matter same as that in Example 1 was continuously dried at atmospheric pressure by using a self-cleaning type dryer manufactured by Mitsubishi Heavy Industries Ltd. under the trade name "SCR 100" in the conditions including a temperature of the object to be dried being 200° C., a heating medium temperature of 240° C., and a starting material feed rate of 38 kg/hour, while nitrogen as a carrier was introduced into the system. As a result, no trouble including the adhesion of solid matter to the machinery and equipment took place even after continuous running for a total of 1 hour, and the average content of NMP in the dried solid matter was 750 ppm.

EXAMPLE 4

The solid matter same as that in Example 1 was batchwise vacuum dried by using a self-cleaning type dryer manufactured by Kurimoto Ltd. under the trade name "SC processor SCP series 100" in the conditions including a temperature of the object to be dried being 150° C., a heating medium temperature of 190° C. and pressure of 14 kPa-abs for one hour. As a result, no trouble including the adhesion of solid matter to the machinery and equipment hardly took place thereby enabling continuous drying, and the average content of NMP in the dried solid matter was 550 ppm.

Comparative Example 1

The solid matter same as that in Example 1 was batchwise dried at atmospheric pressure by using a disc dryer manufactured by Hosokawa Micron Co., Ltd. in the conditions including a temperature of the object to be dried being 200° C., and a heating medium temperature of 240° C., while nitrogen as a carrier was introduced into the system. As a result after one hour from the start of drying treatment, agglomerative solidification of the object to be dried took place. At the point of time, the average content of NMP therein was 10% by weight.

Comparative Example 2

The solid matter same as that in Example 1 was batchwise vacuum dried by using a disc dryer manufactured by Hosokawa Micron Co., Ltd. in the conditions including a temperature of the object to be dried being 150° C., a heating medium temperature of 190° C., and pressure of 14 kPa-abs. As a result after one hour from the start of drying treatment, agglomerative solidification of the object to be dried took place. At the point of time, the average content of NMP therein was 12% by weight.

What is claimed is:

1. A process for treating a by-product salt from a polyarylene sulfide which comprises treating a solid mixture containing an aprotic organic solvent and the by-product salt that is formed in the case of producing the polyarylene sulfide by subjecting an alkali metal sulfide and a dihalogenated aromatic compound to polymerization condensation reaction in the aprotic organic solvent, characterized in that said aprotic organic solvent is recovered by dry treating said solid mixture by the use of a dryer having a self-cleaning property.

2. The process according to claim 1, wherein the dryer having a self-cleaning property is a horizontal twin shaft dryer.

3. The process according to claim 2, wherein the horizontal twin shaft dryer is such that each shaft is equipped with a paddle, and the paddles that are attached to the shafts rotate in the same or different direction, keeping a slight clearance therebetween.

4. The process according to claim 1, wherein the alkali metal sulfide is lithium sulfide.

5. The process according to claim 1, wherein the by-product salt is sodium chloride.

6. The process according to claim 1, wherein the aprotic organic solvent is selected from the group consisting of amide compounds, lactam compounds, urea compounds, organosulfur compounds and cyclic organophosphorus compounds.

7. The process according to claim 1, wherein the aprotic organic solvent is N-methyl-2-pyrrolidone.

8. The process according to claim 1, wherein the polyarylene sulfide is a polymer having at least 70 mole % of the repeating unit represented by —Ar—S—, wherein Ar is an arylene group.

9. The process according to claim 1, wherein the dry treatment of the solid mixture is performed at a temperature in the range of 120 to 250° C., a pressure in the range of atmospheric pressure to 0.01 Pa. for a drying treatment time in the range of one to 10 hours.

10. The process according to claim 1, wherein the dry treatment of the solid mixture is performed so that the content of the aprotic organic solvent therein is made to be 1000 ppm or lower.

* * * * *